US007195897B2

(12) United States Patent
Leonhartsberger et al.

(10) Patent No.: US 7,195,897 B2
(45) Date of Patent: Mar. 27, 2007

(54) FEEDBACK-RESISTANT HOMOSERINE TRANSSUCCINYLASES HAVING A MODIFIED C-TERMINUS

(75) Inventors: Susanne Leonhartsberger, München (DE); Christoph Winterhalter, Pöcking (DE); Kerstin Pfeiffer, München (DE); Brigitte Bauer, München (DE)

(73) Assignee: Consortium für elektrochemische Industrie GmbH, Munich (DE)

( * ) Notice: Subject to any disclaimer, the term of this patent is extended or adjusted under 35 U.S.C. 154(b) by 0 days.

(21) Appl. No.: 10/530,844

(22) PCT Filed: Oct. 16, 2003

(86) PCT No.: PCT/EP03/11486

§ 371 (c)(1),
(2), (4) Date: Apr. 8, 2005

(87) PCT Pub. No.: WO2004/038013

PCT Pub. Date: May 6, 2004

(65) Prior Publication Data

US 2006/0160173 A1 Jul. 20, 2006

(30) Foreign Application Priority Data

Oct. 24, 2002 (DE) ................ 102 49 642

(51) Int. Cl.
| | |
|---|---|
| *C12N 9/00* | (2006.01) |
| *C12N 1/20* | (2006.01) |
| *C12N 15/74* | (2006.01) |
| *C12N 15/00* | (2006.01) |
| *C12P 21/06* | (2006.01) |
| *C08B 31/00* | (2006.01) |
| *C07H 21/04* | (2006.01) |

(52) U.S. Cl. ............ 435/113; 435/69.1; 435/106; 435/252.3; 435/252.8; 435/320.1; 435/471; 536/23.2

(58) Field of Classification Search ............ 435/193, 435/69.1, 252.33, 320.1, 113, 106, 252.3, 435/252.8, 471; 536/23.2
See application file for complete search history.

(56) References Cited

U.S. PATENT DOCUMENTS

| 5,120,837 A | 6/1992 | Fotheringham et al. |
|---|---|---|
| 5,698,418 A | 12/1997 | Brunner et al. |
| 2002/0106800 A1 | 8/2002 | Liaw et al. |

FOREIGN PATENT DOCUMENTS

| DE | 10247437 | 4/2004 |
|---|---|---|
| EP | 0745671 | 12/1996 |
| JP | 2000-139471 | 5/2000 |
| JP | 2000139471 A * | 5/2000 |
| WO | 93/09225 | 5/1993 |

OTHER PUBLICATIONS

Schlesinger S. Inhibition of growth of *Escherichia coli* and of homoserine O-transsuccinylase by alpha-methylmethionine. J. Bacteriol., 1967, vol. 94(2): 327-332.*
Nelson et al., Evidence for lateral gene transfer between Archaea and Bacteria from genome sequence of *Themotoga maritima Nature*. 1999, vol. 399: 323-329.*
Goodner et al., Genome sequence of the plant pathogen and biotechnology agent *Agrobacterium tumefaciens* C58. Science 2001, vol. 294: 2323-2328.*
DelVecchio et al., The genome sequence of the facultative intracellular pathogen *Brucella melitensis*. PNAS 2002, vol. 99(1): 443-448.*
Morinaga et al., Agric. Biol. Chem., vol. 46, No. 1, pp. 57-63, 1982.
Duclos et al., "Nucleohde sequence of the MeFA gene encoding Homoserine Trans-succinylase in *Escherichia coli*," Nucleic Acids Res., 101.17, No. 7, p. 2856.
Bourhy et al., Journal of Bacteriology, Jul. 1997, vol. 179, No. 13, pp. 4396-4698.
Schlenk et al, DePulma et al., "The Formation of S-Adenosylmethionine in Yeast", J. Biol. Chem., 1957, pp. 1037-1050.
Shiouki et al., Agric. Biol. Chem., 1989, vol. 53, No. 12, pp. 3269-3274.
Lee et al., "Multimetabolite control at a Biosynthetic Pathway by sequential metaboliks", J. Biol. Chem., 1966, vol. 241, No. 22, pp. 52479-5480.
Kredich et al., The Enzymic Synthesis of L-Cysteine in *Escherichiaidi coli* and *Salmonella hyphimurium*, J. Biol. Chem., 101.241, No. 21, A66, pp. 4955-4965.
Lawrence et al, Journal of Bacteriology, Jan. 1972, vol. 109, No. 1, pp. 8-11.
Greene et al, "Biosynthesis of Mettionine", Neidhaldt F.C., 2$^{nd}$ Eci: ion, Ash Press, Washington DC, 1996, pp. 546-560.
Thomson Derwent abstract corresponding to JP2000-139471A.*
Derwent abstract corresponding to DE 102 47 437 A1.*

* cited by examiner

*Primary Examiner*—Rebecca E. Prouty
*Assistant Examiner*—Ganapathirama Raghu
(74) *Attorney, Agent, or Firm*—Collard & Roe, P.C.

(57) ABSTRACT

The invention relates to a homoserine transsuccinylase, which exhibits reduced sensitivity towards L-methionine or SAM in comparison with a homoserine transsuccinylase wild-type enzyme, whereby the latter comprises an amino acid sequence containing a TyrGlnXaaThrPro sub-sequence, the Thr of said sub-sequence lying between positions 285 and 310 of the amino acid sequence and position 1 being filled by the starter methionine. The inventive homoserine transsuccinylase is characterized in that in comparison with the wild-type enzyme at least 2 amino acids are modified, said modification taking place in the Thr of the sub-sequence or in the C-terminal.

8 Claims, 1 Drawing Sheet

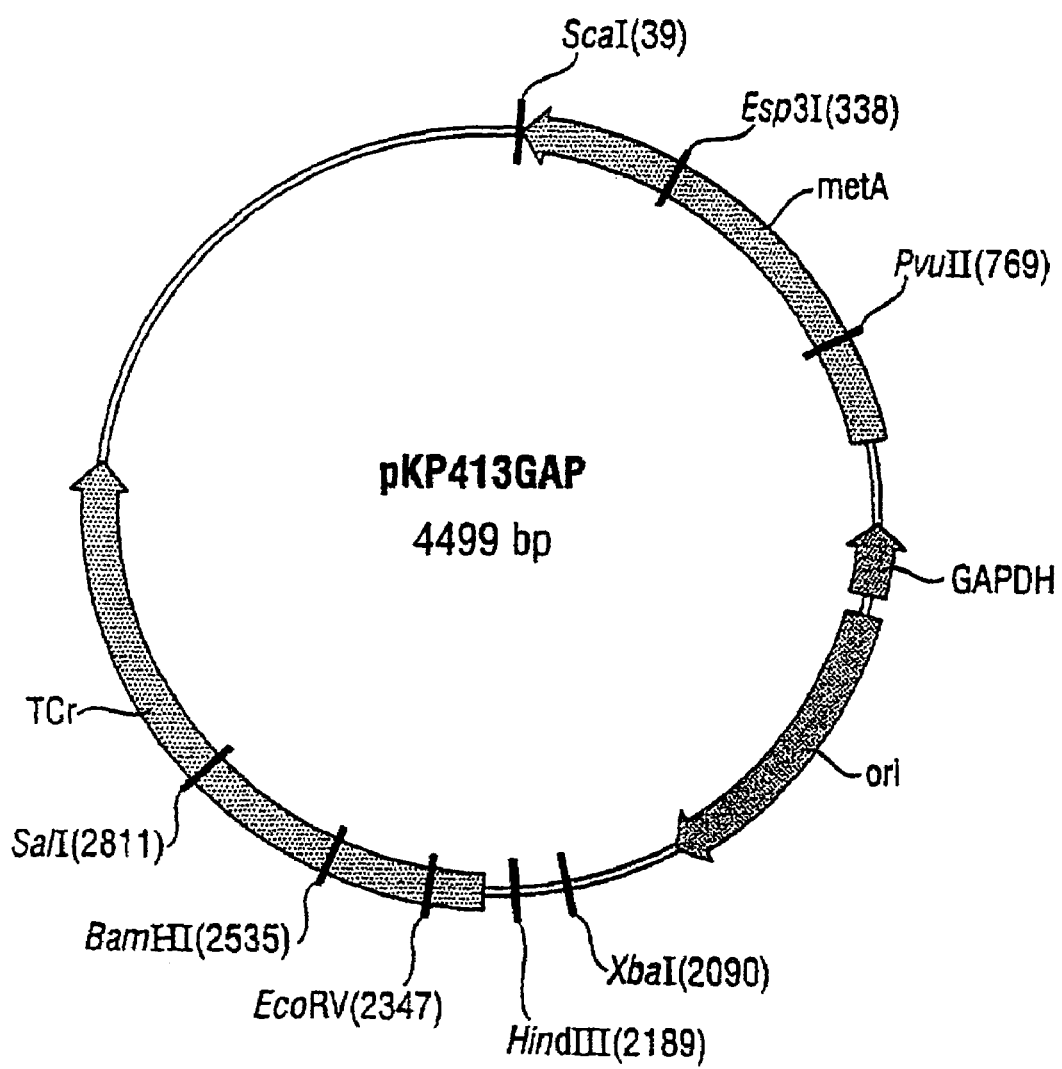

FEEDBACK-RESISTANT HOMOSERINE TRANSSUCCINYLASES HAVING A MODIFIED C-TERMINUS

CROSS REFERENCE TO RELATED APPLICATIONS

Applicants claim priority under 35 U.S.C. §119 of German Application No. 102 49 642.0 filed Oct. 24, 2002. Applicants also claim priority under 35 U.S.C. §365 of PCT/EP2003/011486 filed Oct. 16, 2003. The international application under PCT article 21(2) was not published in English.

The present invention relates to feedback-resistant homoserine transsuccinylases, to microorganism strains containing these enzymes and to their use for preparing L-methionine or S-adenosylmethionine.

Methionine is an amino acid which is essential for humans and many animals. It is, in particular, produced for the feedstuff market and added to animal feed as the racemate. It is synthesized chemically from acrolein and methanethiol by way of 3-(methylthio)-propionaldehyde, which is converted, with hydrogen cyanide, ammonia and carbon dioxide, into D,L-methionine by way of an hydantoin. The racemate can be resolved enzymically.

S-Adenosylmethionine (SAM) is the most important methyl group donor in metabolism and, in the pharmaceutical field, is used in the treatment of depressions, diseases of the liver and arthritis. Methods which have been described for preparing SAM include, in particular, culturing yeasts (Schlenk F. and DePalma R. E., J. Biol. Chem. 1037–1050 (1957), Shiozaki S. et al., Agric. Biol. Chem. 53, 3269–3274 (1989)) in the presence of the precursor L-methionine and chromato-graphically purifying after autolysis.

The microbial synthesis of methionine has been investigated particularly intensively in the bacterium *E. coli* (Greene, R. C., Biosynthesis of Methionine in: Neidhardt F. C., *Escherichia coli* and *Salmonella typhimurium*, Cellular and molecular biology, Second Edition, ASM Press, Washington DC (1996), pages 542–560 and the references contained therein). It consists of a number of enzyme-catalyzed reactions and is strictly regulated. The first steps in the synthesis, from aspartate to homoserine, proceed in parallel with the formation of the amino acids threonine, leucine, isoleucine and valine. The first step which is specific for the synthesis of methionine is the formation of O-succinylhomoserine from succinyl-CoA and homoserine with the elimination of coenzyme A. This reaction is catalyzed by the enzyme homoserine succinyltransferase (homoserine O-transsuccinylase, MetA, EC 2.3.1.46). SAM is synthesized from L-methionine and ATP in one step.

The activity of homoserine transsuccinylase is inhibited in the presence of L-methionine and/or SAM (Lee L.-W. et al., J. Biol. Chem. 241, 5479–5480 (1966)). While this end product inhibition on the one hand prevents an excessive, energy-consuming synthesis of methionine and SAM in the bacterium, it also, on the other hand, stands in the way of the microbial production of these two substances on an industrial scale. The gene encoding homoserine transsuccinylase consists of 930 base pairs (including the stop codon), while the protein encoded by this gene consists of 309 amino acids. The structure of homoserine trans-succinylase has not thus far been elucidated and it is therefore not possible, either, to identify the amino acids which are involved in an end product inhibition.

A known method of increasing the synthesis of metabolic end products is that of using modified enzymes whose activity can no longer be inhibited by the end product of their metabolic pathway (feedback-resistant mutants). Thus, for example, feedback-resistant mutants of 3-deoxy-D-arabinoheptulonic acid 7-phosphate synthase have been prepared for increasing the synthesis of L-tryptophan and L-phenylanaline (EP0745671A2) and feedback-resistant mutants of chorismate mutase/prephenate dehydratase have been generated for increasing the production of phenylalanine (U.S. Pat. No. 5,120,837). The *E. coli* enzyme homoserine transsuccinylase has recently been modified, by mutating the DNA sequence encoding it, such that the activity of the resulting proteins is much less readily inhibited in the presence of L-methionine or SAM (JP2000139471A; DE 10247437 (Application by the same applicant)). The mutations involved were point mutations, that is in each case one amino acid was replaced with another amino acid (JP2000139471A: arginine at position 27 was replaced by cysteine, isoleucine at position 296 was replaced by serine and proline at position 298 was replaced with leucine; DE-10247437: aspartate at position 101 or tyrosine at position 294 was replaced with another natural amino acid). As compared with the wild-type enzyme, the altered homoserine transsuccinylases exhibited improved activity in the presence of the inhibitors L-methionine and/or SAM. Bacterial strains which contain these altered proteins exhibit an increased production of L-methionine.

It is desirable to have available as many variants of homoserine transsuccinylase, which differ in the degree of their activity and in the degree to which they can be inhibited by L-methionine and/or SAM, as possible since the microbial biosynthesis of L-methionine and SAM is highly complex in regard to its course and regulation and, in addition, is interlinked, in a multifaceted manner, with a variety of other metabolic pathways in the cell. It is therefore not possible to make any prediction in advance as to which variant can achieve which effect on the growth of a microorganism strain, on the balance of its vital metabolic processes and on the production of L-methionine and SAM.

The object of the present invention is to make available a broad spectrum of novel variants of homoserine transsuccinylase (MetA protein) which exhibit a feedback resistance in regard to L-methionine and SAM which is increased as compared with that of the wildtype (WT) enzyme.

This object is achieved by means of a homoserine transsuccinylase which, as compared with a homoserine transsuccinylase wild-type enzyme, exhibits a reduced sensitivity towards L-methionine or SAM, with the wild-type enzyme possessing an amino acid sequence which comprises a constituent sequence TyrGlnXaaThrPro, with the Thr of this constituent sequence being between position 285 and 310 of the amino acid sequence and with position 1 being the starting methionine, characterized in that it exhibits a change of at least 2 amino acids as compared with the wild-type enzyme with this change being in the Thr of the constituent sequence or C-terminally thereof.

In the *E. coli* MetA protein, the conserved Thr is at position 297 in the constituent sequence TyrGlnXaaThrPro. (See SEQ ID No. 2). Xaa denotes any arbitrary natural amino acid.

The change is preferably a change of at least 5 amino acids, particularly preferably a change of at least 10 amino acids. The changes can be deletions or insertions.

Thus far, only feedback-resistant homoserine trans-succinylases in which the change as compared with the wild-type is based on a substitution of single amino acids have been disclosed (JP2000139471A). Since the folding of proteins is an extremely complex process and the enzymic activity depends directly on the spatial structure of the proteins, relatively large changes in a protein result in most cases in a loss of activity. However, it has been found, surprisingly, that the multiple changes, in accordance with the invention, in the carboxyterminal moiety of MetA lead to a reduction in the ability of L-methionine and SAM to exert feedback inhibition.

A homoserine transsuccinylase according to the invention exhibits a resistance toward the inhibitors SAM and/or L-methionine which is superior to that of the wild-type enzyme. Preferably, it exhibits a resistance of the homoserine transsuccinylase toward methionine and/or SAM which is at least 2-fold that of the wild type. Particularly preferably, a homoserine transsuccinylase according to the invention has a resistance toward methionine and/or SAM which is 10-fold that of the wild type, particularly preferably a resistance which is increased 50-fold.

Particularly preferably, the protein sequence of a homoserine transsuccinylase according to the invention contains one of the mutations listed in table 1.

A homoserine transsuccinylase according to the invention can be obtained, for example, by expressing a DNA sequence which encodes a homoserine transsuccinylase according to the invention.

The present invention consequently also relates to a DNA sequence which encodes a homoserine trans-succinylase according to the invention.

Such a DNA sequence can be obtained by mutating at least one base in one or more codons of a MetA gene, characterized in that the altered base(s) is/are located in the 3' region starting with the codon for threonine, Thr, in the constituent sequence TyrGlnXaaThrPro, with the Thr in this sequence being located between positions 285 and 310. In the E. coli MetA protein, the Thr of the constituent sequence is located at position 297 (see SEQ ID No. 2).

In that which follows, a DNA sequence according to the invention is designated a feedback-resistant MetA allele. Within the context of the present invention, those genes which, in an analysis using the BESTFIT algorithm (GCG Wisconsin Package, Genetics Computer Group (GCG) Madison, Wisconsin), exhibit a sequence identity of more than 50% with the E. coli WT metA gene are also to be understood as being metA alleles. In precisely the same way, proteins which have a sequence identity of more than 50% with the E. coli wild-type homoserine transsuccinylase (BESTFIT algorithm, GCG Wisconsin Package, Genetics Computer Group (GCG) Madison, Wisconsin), and which possess homoserine transsuccinylase activity, are to be understood as being homoserine transsuccinylases.

The DNA sequence of a metA allele according to the invention preferably contains one of the mutations listed in table 1.

MetA alleles according to the invention can be prepared, for example, by means of nonspecific mutagenesis or targeted mutagenesis, from starting material which is described below. Nonspecific mutations within said DNA region can be produced, for example, by means of chemical agents (e.g. 1-methyl-3-nitro-1-nitrosoguanidine, ethyl methanesulfonic acid, and the like) and/or by means of physical methods and/or by means of PCR reactions carried out under defined conditions, and/or by means of amplifying the DNA in mutator strains (e.g. XL1 red). Methods for introducing mutations at specific positions within a DNA fragment are known. Another possibility of generating feedback-resistant metA alleles consists in combining different, feedback resistance-inducing mutations to give rise to multiple mutants possessing new properties.

The DNA of a wild-type metA gene is preferably used as the starting material for the mutagenesis. The metA gene to be mutated can be encoded chromosomally or extrachromosomally. The abovementioned mutagenesis methods are used to modify one or more nucleotides of the DNA sequence such that the protein which is now encoded by the gene possesses multiple mutations according to the invention.

The techniques which have been described can be used to introduce one or more mutations in said DNA region in any arbitrary metA gene. These mutations result in the encoded homoserine transsuccinylase possessing an amino acid sequence which leads to feedback resistance in relation to SAM and/or L-methionine.

After the mutagenesis, which has, for example, been carried out as described, the mutants possessing the desired phenotype are selected, for example by determining the extent of the sensitivity of the mutated homoserine transsuccinylases to L-methionine and/or SAM.

The invention also relates to microorganisms which contain feedback-resistant metA alleles. These microorganism strains are characterized by the fact that they possess a L-methionine metabolism or SAM metabolism which is at least deregulated by a feedback-resistant metA allele. Since this metabolism proceeds by the same route, which is known per se, in all microorganisms, and the techniques to be used for producing the strains according to the invention are well-known, for example from standard textbooks, and applicable to all microorganisms, strains according to the invention can be prepared from any arbitrary microorganisms. Bacteria are preferred and suitable for producing a strain according to the invention. Gram-negative bacteria, in particular E. coli, are particularly preferably suitable.

The invention furthermore relates to the preparation of L-methionine or SAM by culturing microorganisms according to the invention and also to the use of microorganisms according to the invention for preparing products which contain methionine (such as methionine-containing peptides) or which are derived, in the metabolism of the microorganisms, from L-methionine or SAM (such as polyamines, lipoic acid, biotin or quinones). In addition, microorganisms according to the invention which produce SAM in greater quantities than does the wild type can be used for preparing products which are formed by transferring the methyl group from SAM.

In order to express the modified homoserine trans-succinylase enzyme, the feedback-resistant metA alleles are transformed into a host strain using customary methods.

Any method which enables the activity of the enzyme to be determined in the presence of L-methionine or SAM can be used for determining the sensitivity of the homoserine transsuccinylase to L-methionine and/or SAM. For example, the homoserine transsuccinylase activity can be determined by following the method described by Kredich and Tomkins for determining the activity of serine acetyltransferases (Kredich N. M. and Tomkins G. M., J. Biol. Chem. 241, 4955–4965 (1966)). The enzyme activity is measured in an assay sample which contains homoserine and succinyl-CoA. The reaction is started by adding enzyme and monitored in a spectrophotometer by way of the decrease in the extinction at 232 nm which results from cleavage of the thioester bond in the succinyl-coenzyme A. The described test is suitable for determining the sensitivity of the homoserine transsuccinylases to methionine. The inhibition of homo-serine transsuccinylase activity is tested in the presence of different concentrations of L-methionine in the reaction mixture. The catalytic activity of the different homoserine transsuccinylases is determined in the presence and absence of L-methionine, with these data being used to calculate the inhibition constant Ki, which describes the concentration of inhibitor at which the activity is only 50% of that which can be measured in the absence of the inhibitor.

In order to determine the sensitivity of the activity of the different homoserine transsuccinylases to SAM, it is possible, for example, to carry out an activity test as described in Lee L. W. et al., J. Biol. Chem. 241, 5479–5480 (1966). In this method, the enzyme extract is incubated with homoserine and succinyl-CoA. After various times, a part of the test assay sample is stopped by adding it to a mixture of ethanol, water, and 5,5'-dithiobis(2-nitrobenzoic acid). The absorption is determined photometrically at 412 nm. The described test is suitable, for example, for determining the sensitivity of the homoserine transsuccinylases to SAM. The inhibition of the homoserine transsuccinylase activity is tested in the presence of different concentrations of SAM in the reaction mixture. The catalytic activity of the different homoserine trans-succinylases is determined in the presence and absence of SAM and the inhibition constant Ki is calculated from these data.

Preference is as a rule given to a homoserine transsuccinylase which has a reduced sensitivity to L-methionine and/or SAM while possessing a catalytic activity which is unaltered. For other purposes, it may be desirable for the L-methionine and/or SAM sensitivity and the catalytic activity to be reduced simultaneously.

A feedback-resistant metA allele can be expressed under the control of its own promoter, which is located upstream of the metA gene, or by using other suitable promoter systems which are known to the skilled person. In this connection, the corresponding gene can be present, under the control of such a promoter, either in one or more copies on the chromosome of the host organism or on a vector, preferably a plasmid. The invention therefore also relates to a plasmid, characterized in that it contains a feedback-resistant metA allele according to the invention together with a promoter.

For the cloning, it is possible to use vectors which already contain genetic elements (e.g. constitutive or regulable promoters, terminators) which enable the gene encoding a homoserine transsuccinylase to be expressed either continuously or in a controlled, inducible manner. In addition, other regulatory elements, such as ribosomal binding sites and termination sequences, and also sequences which encode selective markers and/or reporter genes, are present on an expression vector. The expression of these selection markers facilitates identification of transformants. Suitable selection markers are genes which, for example, encode resistance to ampicillin, tetracycline, chloramphenicol, kanamycin and other antibiotics. If the metA allele according to the invention is to be replicated extrachromosomally, the plasmid vector should preferably contain an origin of replication. Particular preference is given to plasmid vectors such as the E. coli vectors pACYC184, pUC18, pBR322 and pSC101 and their derivatives. Examples of suitable inducible promoters are the lac, tac, trc, lambda PL, ara and tet promoters or sequences which are derived therefrom. The constitutive expression of a GAPDH promoter is preferred. In a particularly preferred embodiment of the present invention, the genes encoding the homoserine trans-succinylase are under the control of the GAPDH promoter in a plasmid which is derived from pACYC184. The strategies for integrating genes into the chromosome are prior art.

A suitable host strain is transformed with an expression vector which contains the transcription unit which encodes a L-methionine-insensitive and/or SAM-insensitive homoserine transsuccinylase. Strains which contain L-methionine-sensitive and/or SAM-sensitive proteins, such as bacteria, are used as host strains.

The host strain which is preferably used is an E. coli wild-type strain or a strain in which the endogenous metA gene has been inactivated, such as E. coli strain DL41, CGSC strain collection No. 7177. These strains are complemented with a metA gene according to the invention. Additional measures can be used to increase the ability of a strain according to the invention to produce L-methionine or SAM microbially. For example, it is possible, for this purpose, to use strains in which the metJ gene, which encodes a repressor of the methionine metabolism genes, is no longer expressed (JP2000139471A). Furthermore, there is the possibility of generating homoserine transsuccinylases which are improved over and above this by combining the mutants according to the invention with other mutations, for example with the amino acid substitutions which are specified in DE 10247437 or in JP2000139471A.

L-Methionine or SAM is preferably produced by culturing a microorganism strain according to the invention. For this, the microorganism strain is cultured, for example, in a fermenter in a nutrient medium which contains a suitable carbon source and a suitable energy source as well as other additives.

The substances, such as L-methionine or SAM, which are formed during the fermentation can subsequently be purified.

BRIEF DESCRIPTION OF THE DRAWING

FIG. 1 shows plasmid PKP413GAP containing the E. coli wild-type metA gene under the control of the GAPDH promoter.

DETAILED DESCRIPTION OF EXAMPLES

The following examples serve to provide further clarification of the invention. All the molecular biological methods employed, such as polymerase chain reaction, isolation and purification of DNA, modification of DNA with restriction enzymes, Klenow fragment and ligase, transformation, etc., were carried out in the manner known to the skilled person, in the manner described in the literature or in the manner recommended by the respective manufacturers.

EXAMPLE 1

Generating Feedback-resistant Homoserine Trans-succinylases by Altering the Carboxyterminal Moiety of the metA Structural Gene The plasmid pKP413GAP, which contains the E. coli wild-type metA gene under the control of the GAPDH promoter and is deposited in the Deutsche Sammlung fur Mikroorganismen und Zellkulturen [German Collection of Microorganisms and Cell Cultures] in Brunswick under the number DSM 15221, (FIG. 1) was used as the starting plasmid. Employing pKP413GAP as the substrate, an inverse polymerase chain reaction was carried out using Vent Polymerase (New England Biolabs) in accordance with the rules known to the skilled person. The 5'-phosphorylated oligonucleotides metAde11, having the sequence 5'-CTATTTGTTAGTGAATAATAGTACTGAGCTCTGG-3' (SEQ ID No. 3), and metAde12, having the sequence 5'-CTGGTGGATATATGAGATCTGGTAGACGTAATAG-3' (SEQ ID No. 4), served as primers. The product, which was about 4.3 kb in size, was isolated electrophoretically and purified using a QIAquick gel extraction kit (Qiagen) in accordance with the manufacturer's instructions. After that, an intramolecular ligation using T4 DNA ligase was carried out in accordance with the manufacturer's instructions. *E. coli* cells of the strain DH5α were transformed by the $CaCl_2$ method in the manner known to the skilled person. The transformation mixture was spread on LB tetracycline agar plates (10 g of Trypton/1, 5 g of yeast extract/1, 10 g of NaCl/1, 15 g of agar/1, 15 mg of tetracycline/1) and the plates were incubated overnight at 37° C. The desired transformants were identified by means of a restriction analysis after plasmid isolation had been carried out using a QIAprep Spin Miniprep kit (Qiagen). The region between the Esp3I and ScaI cleavage sites was sequenced and isolated and inserted into a pKP413GAP plasmid which had been treated with the same enzymes. The resulting plasmid, pBaBmetAdel, contains the *E. coli* metA structural gene which is under the control of the GAPDH promoter and which possesses, at its 3' end, the alteration, as compared with the wild-type, which is shown in table 1. The altered amino acid sequence of the protein encoded by this gene is likewise depicted in table 1.

A polymerase chain reaction using the oligonucleotides metAext1, having the sequence 5'-TGGTGGATATATGAGATCTGGTAGACGTAATAG-3', (SEQ ID No. 5), and metAdel1, having the sequence 5'-CTATTTGTTAGTGAATAATAGTACTGAGCTCTGG-3', (SEQ ID No. 3), was employed to generate the plasmid pBaBmetAext by means of a method which is analogous to the method described above.

A polymerase chain reaction using the oligonucleotides metAext1, having the sequence:

5'-TGGTGGATATATGAGATCTGGTAGACGTAATAG-3', (SEQ ID No. 5), and metAext2, having the sequence 5'-GTATTTGTTAGTGAATAATAGTACTGAGCTCTGG-3', (SEQ ID No. 6), was employed to generate the plasmid pBaBmetAext2.

The changes in the metA structural gene, as compared with the wild type, are shown in table 1.

EXAMPLE 2

Activity of the Homoserine Transsuccinylase Mutants, and Feedback Resistance in Regard to L-methionine The activity, and the influence of L-methionine on the activity, of the different homoserine transsuccinylases were determined by means of an enzyme test using cell extracts in which the respective proteins had been produced. For this, the corresponding plasmids, encoding altered homoserine transsuccinylases, were introduced, by transformation, into the *E. coli* strain W3110 (ATCC 27325) using methods known to the skilled person. The transformation mixture was spread on LB-tetracycline agar plates (10 g of tryptone/1, 5 g of yeast extract/1, 5 g of NaCl/1, 15 g of agar/1 and 15 mg of tetracycline/1) and incubated at 37° C. overnight. The resulting transformants were grown in SM1 medium (for 1 l of medium: $CaCl_2 \times 2$ $H_2O$, 0.0147 g, $MgSO_4 \times 7$ $H_2O$, 0.3 g, $Na_2MoO_4 \times 2$ $H_2O$, 0.15 mg, $H_3BO_3$, 2.5 mg, $CoCl_2 \times 6$ $H_2O$, 0.7 mg, $CuSO_4 \times 5$ $H_2O$, 0.25 mg, $MnCl_2 \times 4$ $H_2O$, 1.6 mg, $ZnSO_4 \times 7$ $H_2O$, 0.3 mg, $KH_2PO_4$, 3.0 g, $K_2HPO_4$, 12.0 g, $(NH_4)_2SO_4$, 5 g, NaCl, 0.6 g, $FeSO_4 \times 7$ $H_2O$, 0.002 g, $Na_3$-citrate$\times 2$ $H_2O$, 1 g, glucose, 5 g, tryptone, 1 g, yeast extract, 0.5 g), centrifuged down at an absorption of approx. 0.8 at 600 nm, washed in 50 mM Tris pH 7.5, and centrifuged down once again. The cells were resuspended in 50 mM Tris/Cl, pH 7.5, 2 mM dithiothreitol, 0.5 mM phenylmethylsulfonyl fluoride and disrupted in a French press. The supernatant from a further centrifugation was used as the enzyme extract in the test. The enzyme activity was determined, in a mixture containing 50 mM Tris/Cl, pH 7.6, 1 mM homoserine and 0.1 mM succinyl-CoA, by photometrically quantifying, by means of the decrease in the extinction at 232 nm, the coenzyme A formed in the reaction, following the method described by Kredich and Tomkins for determining the activity of serine acetyl-transferases (Kredich N. M. and Tomkins G. M., J. Biol. Chem. 241, 4955–4965 (1966)). The effect of added L-methionihe on the activity was determined and the inhibitability was quantified as a Ki value. The Ki which is determined is the concentration of L-methionine at which the activity of the homoserine transsuccinylase is only 50% of its activity in the absence of L-methionine.

TABLE 1

Starting plasmid (SP) and also plasmids containing metA variants having an altered carboxy-terminus

| Plasmid | Bases from 889 onwards in the metA structural gene | Amino acids from 297 onwards in the MetA protein |
| --- | --- | --- |
| pKP413GAP (SP) | ACGCCATACGATCTACGGCACATGAATCCAACGCTGGATTAA (segment of the SEQ ID No. 1 sequence from bp 889 to 930) | ThrProTyrAspLeuArgHisMetAsnProThrLeuAsp (segment of the SEQ ID No. 2 sequence from amino acid 297 to 309) |
| pBaBmetAdel | TCATATATCCACCAGCTATTTGTTAGTGAATAA (SEQ ID No. 7) | SerTyrIleHisGlnLeuPheValSerGlu (SEQ ID No. 8) |
| pBaBmetAext | TCATATATCCACCACTATTTGTTAGTGAATAATAGTACTGAGCTCTG GATGCATACGCGTTTAATTAAGCGGCCGCACTGCGATGAGTGGCAGG GCGGGGCG (SEQ ID No. 9) | SerTyrIleHisHisTyrLeuLeuValAsnAsnSerThrGlu LeuTrpMetHisThrArgLeuIleLysArgProHisCysAsp GluTrpGlnGlyGlyAla (SEQ ID No. 10) |
| pBaBmetAext2 | TCATATATCCACCAGTATTTGTTAGTGAATAATAGTACTGAGCTCTG GATGCATACGCGTTTAATTAAGCGGCCGCACTGCGATGAGTGGCAGG GCGGGGCG (SEQ ID No. 11) | SerTyrIleHisGlnTyrLeuLeuValAsnAsnSerThrGlu LeuTrpMetHisThrArgLeuIleLysArgProHisCysAsp GluTrpGlnGlyGlyAla (SEQ ID No. 12) |

All the homoserine transsuccinylase mutants exhibit a feedback resistance in regard to L-methionine which is elevated as compared with that of the wild type. Table 2 summarises the results.

TABLE 2

Activities of the WT enzyme and the homoserine transsuccinylase mutants, and feedback resistances in regard to L-methionine.

| Plasmid | Activity (U/mg) | Activity (%) * in the presence of 1 mM L-methionine | L-Methionine Ki (mM) |
|---|---|---|---|
| pKP413GAP | 0.155 | 2 | 0.05 |
| pBaBmetAde1 | 0.042 | 95 | 16 |
| pBaBmetAext | 0.011 | 91 | 10 |
| pBaBmetAext2 | 0.045 | 90 | 5 |

* Activity in the absence of L-methionine corresponds to 100%.

EXAMPLE 3

Feedback Resistance of the Homoserine Transsuccinylases in Regard to SAM

The influence of SAM on the activities of the different homoserine transsuccinylases was determined by quantifying the activity in the presence of different concentrations of SAM (Cl salt, Sigma). The cell extracts were grown and prepared as described in Example 2. The activity test was carried out as described in Lee L. W. et al., J. Biol. Chem. 241, 5479–5480 (1966), with the enzyme extract being incubated with 50 mM potassium phosphate buffer, pH 7.5, 3 mM homoserine and 0.3 mM succinyl-CoA. After various times, 100 µl volumes of test mixture were stopped by adding them in each case to a mixture of 400 µl of ethanol, 400 µl of water and 100 µl of 10 mM 5,5'-dithiobis(2-nitrobenzoic acid). After the resulting mixture had been incubated at room temperature for 5 minutes, the absorption was determined photometrically at 412 nm. After the protein concentration had been determined, the enzyme activity was calculated using the extinction coefficient. The Ki was determined as a measure of the ability of SAM to inhibit the activity.

TABLE 3

Activities of the homoserine transsuccinylase mutants, and feedback resistances in regard to SAM.

| Plasmid | Activity (U/mg) | Activity (%) * in the presence of 1 mM SAM | SAM Ki (mM) |
|---|---|---|---|
| pKP413GAP | 0.62 | 0.5 | 0.2 |
| pBaBmetAde1 | 0.25 | 95 | 9 |
| pBaBmetAext | 0.082 | 75 | 4 |
| pBaBmetAext2 | 0.173 | 99 | 16 |

* Activity in the absence of SAM corresponds to 100%.

---

The invention claimed is:

1. A homoserine transsuccinylase which, as compared with a homoserine transsuccinylase wild-type enzyme, exhibits a reduced sensitivity toward L-methionine or S-Adenosylmethionine (SAM), with the wild-type enzyme possessing an amino acid sequence of SEQ ID NO: 2 which comprises a constituent sequence TyrGlnXaaThrPro, with the Thr of this constituent sequence at position 297 onward being replaced by one of the mutations listed in Table 1.

2. A homoserine transsuccinylase as claimed in claim 1, wherein it exhibits a change of at least 5 amino acids.

3. A homoserine transsuccinylase as claimed in claim 1, wherein it exhibits a resistance toward the inhibitors SAM and/or L-methionine which is increased (increased Ki) at least 2-fold as compared with that of the wild-type enzyme.

4. A metA allele which encodes a homoserine transsuccinylase as claimed in claim 1.

5. A plasmid, wherein it contains a metA allele as claimed in claim 4 together with a promoter.

6. A microorganism strain, wherein it contains a metA allele as claimed in claim 4.

7. A microorganism strain as claimed in claim 6, wherein it is a Gram-negative bacterial strain.

8. A method for preparing L-methionine or SAM by culturing a microorganism strain as claimed in claim 6.

* * * * *

SEQUENCE LISTING

<160> NUMBER OF SEQ ID NOS: 12

<210> SEQ ID NO 1
<211> LENGTH: 930
<212> TYPE: DNA
<213> ORGANISM: Escherichia coli
<220> FEATURE:
<221> NAME/KEY: CDS
<222> LOCATION: (1)..(930)
<300> PUBLICATION INFORMATION:
<301> AUTHORS: Blattner, F. R.
<302> TITLE: The complete genome sequence of Escherichia coli K-12.
<303> JOURNAL: Science
<304> VOLUME: 277
<305> ISSUE: 533
<306> PAGES: 1453-1474
<307> DATE: 1997

<400> SEQUENCE: 1

```
atg ccg att cgt gtg ccg gac gag cta ccc gcc gtc aat ttc ttg cgt      48
Met Pro Ile Arg Val Pro Asp Glu Leu Pro Ala Val Asn Phe Leu Arg
  1               5                  10                  15 gaa gaa aac gtc ttt gtg atg aca act tct cgt gcg tct ggt cag gaa      96
Glu Glu Asn Val Phe Val Met Thr Thr Ser Arg Ala Ser Gly Gln Glu
             20                  25                  30 att cgt cca ctt aag gtt ctg atc ctt aac ctg atg ccg aag aag att     144
Ile Arg Pro Leu Lys Val Leu Ile Leu Asn Leu Met Pro Lys Lys Ile
         35                  40                  45 gaa act gaa aat cag ttt ctg cgc ctg ctt tca aac tca cct ttg cag     192
Glu Thr Glu Asn Gln Phe Leu Arg Leu Leu Ser Asn Ser Pro Leu Gln
     50                  55                  60 gtc gat att cag ctg ttg cgc atc gat tcc cgt gaa tcg cgc aac acg     240
Val Asp Ile Gln Leu Leu Arg Ile Asp Ser Arg Glu Ser Arg Asn Thr
```

|  |  |
|---|---:|
| ccc gca gag cat ctg aac aac ttc tac tgt aac ttt gaa gat att cag<br>Pro Ala Glu His Leu Asn Asn Phe Tyr Cys Asn Phe Glu Asp Ile Gln<br>               85                       90                   95 | 288 |
| gat cag aac ttt gac ggt ttg att gta act ggt gcg ccg ctg ggc ctg<br>Asp Gln Asn Phe Asp Gly Leu Ile Val Thr Gly Ala Pro Leu Gly Leu<br>              100                    105                  110 | 336 |
| gtg gag ttt aat gat gtc gct tac tgg ccg cag atc aaa cag gtg ctg<br>Val Glu Phe Asn Asp Val Ala Tyr Trp Pro Gln Ile Lys Gln Val Leu<br>          115                    120                  125 | 384 |
| gag tgg tcg aaa gat cac gtc acc tcg acg ctg ttt gtc tgc tgg gcg<br>Glu Trp Ser Lys Asp His Val Thr Ser Thr Leu Phe Val Cys Trp Ala<br>130                    135                    140 | 432 |
| gta cag gcc gcg ctc aat atc ctc tac ggc att cct aag caa act cgc<br>Val Gln Ala Ala Leu Asn Ile Leu Tyr Gly Ile Pro Lys Gln Thr Arg<br>145                    150                    155                  160 | 480 |
| acc gaa aaa ctc tct ggc gtt tac gag cat cat att ctc cat cct cat<br>Thr Glu Lys Leu Ser Gly Val Tyr Glu His His Ile Leu His Pro His<br>              165                    170                  175 | 528 |
| gcg ctt ctg acg cgt ggc ttt gat gat tca ttc ctg gca ccg cat tcg<br>Ala Leu Leu Thr Arg Gly Phe Asp Asp Ser Phe Leu Ala Pro His Ser<br>          180                    185                  190 | 576 |
| cgc tat gct gac ttt ccg gca gcg ttg att cgt gat tac acc gat ctg<br>Arg Tyr Ala Asp Phe Pro Ala Ala Leu Ile Arg Asp Tyr Thr Asp Leu<br>          195                    200                  205 | 624 |
| gaa att ctg gca gag acg gaa gaa ggg gat gca tat ctg ttt gcc agt<br>Glu Ile Leu Ala Glu Thr Glu Glu Gly Asp Ala Tyr Leu Phe Ala Ser<br>210                    215                    220 | 672 |
| aaa gat aag cgc att gcc ttt gtg acg ggc cat ccc gaa tat gat gcg<br>Lys Asp Lys Arg Ile Ala Phe Val Thr Gly His Pro Glu Tyr Asp Ala<br>225                    230                    235                  240 | 720 |
| caa acg ctg gcg cag gaa ttt ttc cgc gat gtg gaa gcc gga cta gac<br>Gln Thr Leu Ala Gln Glu Phe Phe Arg Asp Val Glu Ala Gly Leu Asp<br>              245                    250                  255 | 768 |
| ccg gat gta ccg tat aac tat ttc ccg cac aat gat ccg caa aat aca<br>Pro Asp Val Pro Tyr Asn Tyr Phe Pro His Asn Asp Pro Gln Asn Thr<br>          260                    265                  270 | 816 |
| ccg cga gcg agc tgg cgt agt cac ggt aat tta ctg ttt acc aac tgg<br>Pro Arg Ala Ser Trp Arg Ser His Gly Asn Leu Leu Phe Thr Asn Trp<br>          275                    280                  285 | 864 |
| ctc aac tat tac gtc tac cag atc acg cca tac gat cta cgg cac atg<br>Leu Asn Tyr Tyr Val Tyr Gln Ile Thr Pro Tyr Asp Leu Arg His Met<br>290                    295                    300 | 912 |
| aat cca acg ctg gat taa<br>Asn Pro Thr Leu Asp<br>305 | 930 |

<210> SEQ ID NO 2
<211> LENGTH: 309
<212> TYPE: PRT
<213> ORGANISM: Escherichia coli

<400> SEQUENCE: 2

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

```
Glu Thr Glu Asn Gln Phe Leu Arg Leu Leu Ser Asn Ser Pro Leu Gln
 50                  55                  60

Val Asp Ile Gln Leu Leu Arg Ile Asp Ser Arg Glu Ser Arg Asn Thr
 65                  70                  75                  80

Pro Ala Glu His Leu Asn Asn Phe Tyr Cys Asn Phe Glu Asp Ile Gln
                 85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
            115                 120                 125

Glu Trp Ser Lys Asp His Val Thr Ser Thr Leu Phe Val Cys Trp Ala
130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
            195                 200                 205

Glu Ile Leu Ala Glu Thr Glu Glu Gly Asp Ala Tyr Leu Phe Ala Ser
210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
            275                 280                 285

Leu Asn Tyr Tyr Val Tyr Gln Ile Thr Pro Tyr Asp Leu Arg His Met
290                 295                 300

Asn Pro Thr Leu Asp
305

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence:
      Primer for PCR

<400> SEQUENCE: 3
ctatttgtta gtgaataata gtactgagct ctgg                              34

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence:
      Primer for PCR

<400> SEQUENCE: 4
ctggtggata tatgagatct ggtagacgta atag                              34

<210> SEQ ID NO 5
```

```
<211> LENGTH: 33
<212> TYPE: DNA
<213> ORGANISM: Artificial Sequence
<220> FEATURE:
<223> OTHER INFORMATION: Description of Artificial Sequence:
      Primer for PCR

<400> SEQUENCE: 5
tggtggatat atgagatctg gtagacgtaa tag                              33

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence:
      Primer for PCR

<400> SEQUENCE: 6
gtatttgtta gtgaataata gtactgagct ctgg                             34

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence:
      Changes in Met A structural gene

<400> SEQUENCE: 7
tcatatatcc accagctatt tgttagtgaa taa                              33

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Changes in
      protein encoded by altered Met A structural gene

<400> SEQUENCE: 8

Ser Tyr Ile His Gln Leu Phe Val Ser Glu
 1               5                  10

<210> SEQ ID NO 9
<211> LENGTH: 102
<212> TYPE: DNA
<213> ORGANISM: Artificial Sequence
<220> FEATURE:
<223> OTHER INFORMATION: Description of Artificial Sequence: Changes in
      Met A structural gene

<400> SEQUENCE: 9
tcatatatcc accactattt gttagtgaat aatagtactg agctctggat gcatacgcgt    60
ttaattaagc ggccgcactg cgatgagtgg cagggcgggg cg                      102

<210> SEQ ID NO 10
<211> LENGTH: 34
<212> TYPE: PRT
<213> ORGANISM: Artificial Sequence
<220> FEATURE:
<223> OTHER INFORMATION: Description of Artificial Sequence: Changes in
      Protein encoded by altered Met A structural gene

<400> SEQUENCE: 10

Ser Tyr Ile His His Tyr Leu Leu Val Asn Asn Ser Thr Glu Leu Trp
 1               5                  10                  15
```

```
Met His Thr Arg Leu Ile Lys Arg Pro His Cys Asp Glu Trp Gln Gly
            20                  25                  30

Gly Ala

<210> SEQ ID NO 11
<211> LENGTH: 102
<212> TYPE: DNA
<213> ORGANISM: Artificial Sequence
<220> FEATURE:
<223> OTHER INFORMATION: Description of Artificial Sequence: Changes in
      Met A structural gene

<400> SEQUENCE: 11
tcatatatcc accagtattt gttagtgaat aatagtactg agctctggat gcatacgcgt        60
ttaattaagc ggccgcactg cgatgagtgg cagggcgggg cg                         102

<210> SEQ ID NO 12
<211> LENGTH: 34
<212> TYPE: PRT
<213> ORGANISM: Artificial Sequence
<220> FEATURE:
<223> OTHER INFORMATION: Description of Artificial Sequence: Changes in
      protein encoded by altered Met A structural gene

<400> SEQUENCE: 12

Ser Tyr Ile His Gln Tyr Leu Leu Val Asn Asn Ser Thr Glu Leu Trp
 1               5                  10                  15

Met His Thr Arg Leu Ile Lys Arg Pro His Cys Asp Glu Trp Gln Gly
            20                  25                  30

Gly Ala
```